United States Patent [19]

McConnell

[11] Patent Number: 5,571,157
[45] Date of Patent: Nov. 5, 1996

[54] ENDOCARDIAL LEAD WITH REDUCED DIAMETER TIP PORTION AND METHOD FOR MAKING SUCH LEAD

[75] Inventor: Susan M. McConnell, Woodland Hills, Calif.

[73] Assignee: Pacesetter, Inc., Sylmar, Calif.

[21] Appl. No.: 504,207

[22] Filed: Jul. 19, 1995

[51] Int. Cl.$^6$ .................................................. A61N 1/05
[52] U.S. Cl. ........................................... 607/116; 607/122
[58] Field of Search ............................ 128/642; 607/115, 607/116, 119, 122–123

[56] References Cited

U.S. PATENT DOCUMENTS

| | | |
|---|---|---|
| 4,409,994 | 10/1983 | Doring . |
| 4,566,467 | 1/1986 | De Haan .................................. 607/116 |
| 4,576,174 | 3/1986 | Miyazaki et al. ......................... 128/642 |
| 5,014,720 | 5/1991 | Barcel et al. ............................. 607/122 |
| 5,324,326 | 6/1994 | Lubin ....................................... 607/122 |
| 5,385,578 | 5/1995 | Bush et al. ............................... 607/122 |

FOREIGN PATENT DOCUMENTS

| | | | |
|---|---|---|---|
| 2421626 | 9/1978 | France ..................................... 607/122 |
| 3043189 | 11/1980 | Germany ................................. 607/122 |

Primary Examiner—William E. Kamm
Assistant Examiner—George R. Evanisko
Attorney, Agent, or Firm—Harold C. Schloss

[57] ABSTRACT

An endocardial lead assembly, adapted to transmit electrical signals between a proximal end portion of the lead assembly and a distal end portion of the assembly and to thereby stimulate selected body tissue, includes at least two coiled, insulatively coated conductors extending between the proximal and distal end portions for transmitting the electrical signals. The coils of the at least two insulated conductors are contiguous and have substantially the same first outer diameter, one of the coiled conductors having a portion extending through said distal end portion of the lead and being electrically connected to said tip electrode. The remaining conductor(s) terminate at a proximal extremity of the distal end portion, the portion of the one coiled conductor within the distal end portion including contiguous, uninsulated coils having a second outer diameter that is less than the first diameter. The lead assembly includes an insulating sheath of biocompatible material for electrically insulating the at least two coiled conductors from body tissue and fluids.

12 Claims, 1 Drawing Sheet

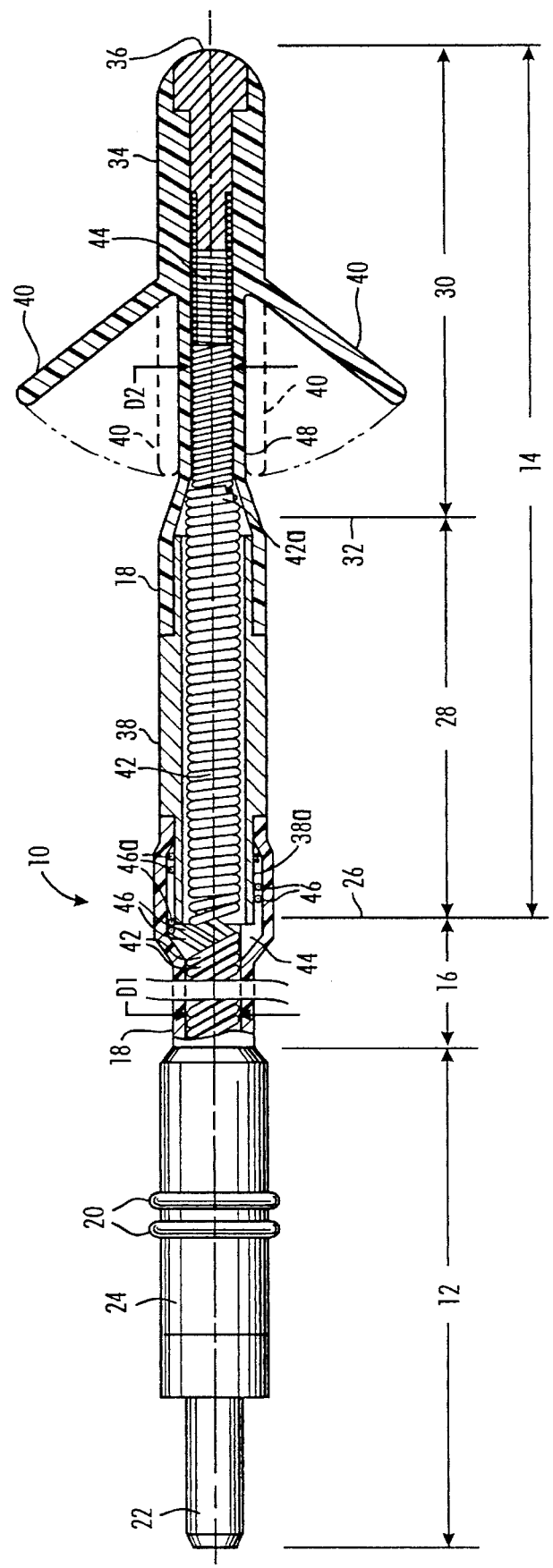

ENDOCARDIAL LEAD WITH REDUCED DIAMETER TIP PORTION AND METHOD FOR MAKING SUCH LEAD

FIELD OF THE INVENTION

The present invention relates generally to lead assemblies for connecting implantable medical devices with selected body tissue to be stimulated by such devices, and more particularly to endocardial leads in which the cross-sectional area of the distal tip portion is minimized.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled conductor surrounded by an insulating tube or sheath of biocompatible material, couples the connector pin at the proximal end with the electrode at the distal end.

The electrode tip of an endocardial lead must be anchored to the heart to prevent it from becoming dislodged or dislocated. A number of methods, both passive and active, have been devised for this purpose. In accordance with one known passive fixation technique, a plurality of flexible tines are molded integrally with the insulative sheath covering the coiled electrical conductors and extend rearwardly at an acute angle relative to the longitudinal axis of the lead. Following implantation of the lead, the tines become entangled in the trabecular network thereby securing the electrode position. Since the tines can flatten against the lead body and thus reduce its diameter, tined leads are often suitable for introduction through small blood veins. Other known passive fixation techniques include collar electrodes which have one or more conical projections of silicon rubber or other biocompatible flexible material behind the electrode tip. Like the tines, the cone becomes entangled in the trabecular network inside the heart, thereby anchoring the electrode tip. In yet another known approach which is advantageous if relocation of the electrode tip becomes necessary, projecting, flexible fins are used to provide stable anchoring.

Irrespective of the passive fixation technique employed, the anchoring section of an endocardial lead is the portion of the tip that has the largest cross sectional area. It is desirable to minimize this area to facilitate passage of the lead through small diameter blood veins by minimizing the resistance to insertion and removal of the lead. It is also desirable to minimize the cross sectional area of the tip portion of the lead so as to reduce the diameter of the introducer sleeve where implantation is effected by means of a lead introducer. Since the purpose of the introducer is to provide direct entry of the endocardial lead into a vessel, it is important to minimize the size of the opening in the vessel so as to minimize trauma at the introduction site. In the case of tined leads, one expedient for minimizing lead cross sectional area is to provide a recessed portion of the insulating sheath just behind the tines. During implantation the recessed portion receives the folded tines which lie flat within that portion and substantial flush with the outer surface of the insulative sheath.

As is known, many of today's intravascular endocardial leads are multipolar in which, besides an electrode at the tip, one or more ring electrodes are incorporated in the distal end portion of the lead for transmitting electrical stimulation pulses from the pulse generator to the heart and/or to transmit naturally occurring sensed electrical signals from the heart to the pulse generator. Thus, by way of example, in a typical bipolar lead having a tip electrode and a ring electrode, two concentric conductor coils with insulation in between are carried within the insulative sheath. One of the conductor coils connects the pulse generator with the tip electrode while the other conductor coil, somewhat shorter than the first conductor coil, connects the pulse generator with the ring electrode positioned behind the tip electrode. More recently, to reduce the outside diameter of multipolar leads, the individual conductors are insulated and instead of being concentric all of the conductor coils are wound on the same diameter. Thus, in a multipolar lead employing this technique, the various coil conductors are interleaved along the same coil diameter thereby helping to reduce the overall diameter of the lead.

Despite the foregoing and other techniques for reducing the cross sectional area of the tip portion of endocardial leads, still further size reduction is desirable.

Accordingly, an overall object of the present invention is to further reduce the cross sectional area of the tip portion of an endocardial lead employing passive fixation means.

SUMMARY OF THE INVENTION

In accordance with one specific, exemplary embodiment of the present invention, there is provided a body implantable lead assembly adapted to transmit electrical signals between a proximal end portion of the lead assembly and a distal end portion of the assembly so as to stimulate selected body tissue. The distal end portion has a proximal extremity, a distal tip and an electrode at the distal tip. At least two coiled, insulatively coated conductors extend between the proximal and distal end portions for transmitting the electrical signals, the coils of the at least two insulated conductors having substantially the same first outer diameter. One of the coiled conductors has a portion extending through the distal end portion of the lead and is electrically connected to the tip electrode. The remaining conductor(s) terminate at the proximal extremity of the distal end portion. The portion of the one coiled conductor within the distal end portion includes uninsulated coils having a second outer diameter that is less than the first diameter. The lead assembly also includes an insulating sheath of biocompatible material for electrically insulating the at least two coiled conductors from body tissue and fluids.

In accordance with another aspect of the present invention, the distal end portion comprises a proximal segment and a distal segment, the proximal segment extending between the proximal extremity of the distal end portion and the distal segment, and the distal segment including the distal tip. The portion of the one conductor within the proximal segment of the distal end portion is insulated. The portion of the one coiled conductor within the distal segment has the uninsulated, contiguous coils having the second outer diameter.

In accordance with another aspect of the present invention there is provided a method for making an endocardial lead assembly of the kind described above. The method includes the steps of winding at least two coiled conductors on a first diameter, each of the conductors including an insulative coating; terminating one of the coiled conductors at the proximal extremity of the distal end portion, the remaining conductor(s) continuing through the distal end portion to the electrode at the distal tip; removing the insulative coating from the remaining conductor(s) along a portion of the conductor(s) immediately adjacent the distal tip; and rewinding the uninsulated portion of the remaining conductor(s) on a second diameter that is less than the first diameter.

BRIEF DESCRIPTION OF THE DRAWINGS

Further objects, features and advantages of the invention will become apparent from the detailed description of the preferred embodiment, below, when read in conjunction with the accompanying drawing in which the single figure is a side view, partly in section, of a bipolar endocardial pacing and sensing lead incorporating the present invention.

DESCRIPTION OF THE PREFERRED EMBODIMENT

The following description presents a preferred embodiment of the invention representing the best mode contemplated for practicing the invention. This description is not to be taken in a limiting sense but is made merely for the purpose of describing the general principles of the invention whose scope is defined by the appended claims. Moreover, the context in which the invention is shown herein, that is, a bipolar pacing and sensing lead, is illustrative only; it will be understood by those skilled in the art that the invention may be used in a wide variety of multipole body implantable lead type.

Referring now to the drawing, there is shown a bipolar, endocardial pacing and sensing lead assembly 10 having a proximal end portion 12, a distal end portion 14 and an intermediate portion 16 connecting the end portions 12 and 14. The lead assembly 10 is covered by a tubular, insulating housing or sheath 18 made of an insulating biocompatible, biostable material such as polyurethane or silicone rubber. The proximal end portion 12 is adapted to be plugged into the socket or receptacle of a cardiac pacemaker (not shown) and for this purpose the elastomeric housing 18 includes longitudinally spaced sets of annular ribs 20 for sealing the pacemaker receptacle against the entry of bodily fluids.

The proximal end portion 12 of the lead assembly 10 includes an electrical connector pin 22 and an electrically conductive ring 24. As is well known, the pin 22 and ring 24 engage corresponding terminals in the receptacle of the cardiac pacemaker. The distal end portion 14 of the lead assembly 10 interfaces with the intermediate portion 16 at a proximal extremity 26 of the distal end portion 14. The distal end portion 14 consists of two segments: a proximal segment 28 and a distal segment 30, the proximal segment 28 extending between the extremity 26 and a proximal extremity 32 of the distal segment 30. The distal segment 30 includes a distal tip 34 incorporating a tip electrode 36, while the proximal segment 28 incorporates a ring-shaped sensor electrode 38. Projecting from the tubular sheath 18 along the distal segment 30 are four equiangularly spaced tines 40 for engaging the heart tissue and urging the tip electrode 36 into contact with the endocardium.

The connector pin 22 on the proximal end portion 12 is hollow and is electrically coupled to the tip electrode 36 by means of a coil conductor 42 enclosed within the tubular sheath 18. In accordance with well-known implantation procedures, a stylet (not shown) is passed through the hollow connector pin 22 and the central cavity or lumen 44 of the associated coil conductors to enable the physician to orient the distal end portion 14 of the lead and to position the tip electrode 36 under fluoroscopy to a desired location in the heart.

The contact ring 24 on the proximal end portion 12 is electrically coupled to the sensing ring electrode 38 by a second coil conductor 46 within the housing 18.

In a manner well known in the art, the coil conductors 42 and 46 have insulative coatings 42a and 46a, respectively, so that they may be wound so as to have substantially the same outer diameter D1, referred to herein sometimes as the first diameter, within the intermediate portion 16 of the lead assembly 10. Moreover, also as well known in the art, each of the coil conductors 42 and 46 may comprise a multifilar conductor for redundancy to provide continued stimulation and sensing in the event one of the conductor strands breaks. Thus, in the example shown in the drawing, each coil conductor 42 and 46 consists of two filaments or strands.

The filaments of the multifilar coil conductor 46 are terminated at the ring sensor electrode 38 which includes a terminal 38a to which all of the filaments of the conductor 46 are electrically connected. As can be seen in the drawing, this connection is made in the vicinity of the proximal extremity 26 of the distal end portion 14. The coil conductor 42 continues through the distal end portion 14 to the tip electrode 36 to which the coil conductor 42 is electrically connected in a fashion well known in the art.

It will be understood that with the termination of the coil conductor 46 at the ring sensor electrode 38, there will remain gaps between adjacent turns of the insulatively coated conductor 42 once occupied by the coil conductor 46. Accordingly, within the proximal segment 28 of the distal end portion 14, the insulated conductor 42 is rewound at a reduced pitch so as to remove the gaps between adjacent turns of the coil to thereby maintain their contiguousness. The outer diameter of the rewound conductor 42 within the proximal segment 28 of the distal end portion 14 will remain approximately the same as the first diameter D1.

The insulation 42a is retained on the conductor 42 within the proximal segment 28 so as to insulate that conductor from the ring sensing electrode 38. Within the distal segment 30 of the distal end portion 14, however, such insulation is no longer needed. Accordingly, in accordance with an important aspect of the invention, within the distal segment 30, the insulation 42a on the coil conductor 42 is removed, permitting the uninsulated conductor 42 to be rewound at a still further reduced pitch to remove the gaps between adjacent coil turns resulting from the removal of the insulation. The uninsulated conductor 42 within the distal segment 30 will accordingly consist of contiguous coil turns having a second outer diameter D2 that is smaller than the first diameter D1 yet still permitting passage of a stylet. As evident from the drawing, the outer diameter of the sheath 18 along the distal segment 30 can be correspondingly reduced so as to provide a small diameter recess 48 for receiving the tines 40 when they fold back during lead introduction to the position shown by the broken lines in the drawing. The cross-sectional area of the distal segment 30 may therefore be reduced and minimized, providing the advantages mentioned earlier.

While the invention has been described in connection with a preferred embodiment, it will be understood that it is not intended to limit the invention thereto, but that it is intended to cover all modifications and alternative constructions falling within the spirit and scope of the invention as expressed in the appended claims.

What is claimed is:

1. A body implantable lead assembly adapted to transmit electrical signals between a proximal end portion of the lead assembly and a distal end portion of the assembly and to thereby stimulate selected body tissue, said distal end portion having a proximal extremity, a distal tip and an electrode at the distal tip, the assembly comprising:

at least two coiled conductors extending between said proximal and distal end portions for transmitting the electrical signals, the coils of the at least two conductors having substantially the same first outer diameter, one of the coiled conductors having a portion extending through said distal end portion of the lead and being electrically connected to said tip electrode, the remaining conductor(s) terminating at the proximal extremity of the distal end portion, the portion of the one coiled conductor within the distal end portion including coils having a second outer diameter that is less than the first diameter; and insulating sheath means of biocompatible material for electrically insulating the at least two coiled conductors from body tissue and fluids.

2. A lead assembly, as defined in claim 1, in which:

said distal end portion comprises a proximal segment and a distal segment, the proximal segment extending between the proximal extremity of the distal end portion and the distal segment, and the distal segment including the distal tip, the portion of the one conductor within the proximal segment of the distal end portion being insulated, the portion of the one conductor within the distal segment being uninsulated.

3. A lead assembly, as defined in claim 2, in which:

said proximal segment of the distal end portion includes a ring sensor electrode electrically connected to said remaining conductor(s).

4. A lead assembly, as defined in claim 3, in which:

the insulating sheath means has a portion insulating the distal segment of the distal end portion, said insulating sheath portion including projecting, foldable tines for anchoring the distal tip electrode, said insulating sheath portion further including a recessed portion along said distal segment for receiving the tines in their folded condition.

5. A body implantable lead assembly adapted to transmit electrical signals between a proximal end portion of the lead assembly and a distal end portion of the assembly and to thereby stimulate selected body tissue, said distal end portion having a proximal extremity, a distal tip and an electrode at the distal tip, the assembly comprising:

at least two coiled, insulated conductors extending between said proximal and distal end portions for transmitting the electrical signals, the coils of the at least two insulated conductors being contiguous and having substantially the same first outer diameter, one of the coiled conductors extending through said distal end portion of the lead and being electrically connected to said tip electrode, the remaining conductor(s) terminating at the proximal extremity of the distal end portion, said distal end portion comprising a proximal segment and a distal segment, the proximal segment extending between the proximal extremity of the distal end portion and the distal segment, and the distal segment including the distal tip, the portion of the one conductor within the proximal segment having contiguous insulated coils having an outer diameter approximately equal to the first diameter, the portion of the one conductor within the distal segment having uninsulated, contiguous coils having a second outer diameter that is less than the first diameter; and insulating sheath means of biocompatible material for electrically insulating the at least two coiled conductors from body tissue and fluids.

6. A lead assembly, as defined in claim 5, in which:

said proximal segment of the distal end portion includes a ring sensor electrode electrically connected to said remaining conductor(s).

7. A lead assembly, as defined in claim 5, in which:

the insulating sheath means has a portion insulating the distal segment of the distal end portion, said insulating sheath portion including projecting, foldable tines for anchoring the distal tip electrode, said insulating sheath portion further including a recessed portion along said distal segment for receiving the tines in their folded condition.

8. A method for making a body implantable lead assembly adapted to transmit electrical signals between a proximal end portion of the lead assembly and a distal end portion of the assembly and to thereby stimulate selected body tissue, said distal end portion having a proximal extremity, a distal tip and an electrode at the distal tip, the method including the steps of:

winding at least two coiled conductors on a first diameter, each of the conductors including an insulative coating;

terminating all but one of the coiled conductors at the proximal extremity of the distal end portion, the one remaining conductor continuing through the distal end portion to the electrode at the distal tip;

removing the insulating coating from the one remaining conductor along a portion thereof immediately adjacent the distal tip; and rewinding the uninsulated portion of the one remaining conductor on a second diameter that is less than the first diameter.

9. A distal end portion of a body implantable lead assembly adapted to transmit electrical signals and to thereby stimulate selected body tissue, said distal end portion having a proximal extremity, a distal tip and an electrode at the distal tip, the distal end portion comprising:

a coiled conductor extending between said proximal extremity and said distal tip, the coiled conductor being electrically connected to said tip electrode, a first portion of the coiled conductor having a first outer diameter, and a second portion of the coiled conductor having a second outer diameter that is less than the first outer diameter, wherein the first portion of the coiled conductor is insulated and the second portion of the coiled conductor is uninsulated.

10. A distal end portion, as defined in claim 9, further comprising:

insulating sheath means of biocompatible material for electrically insulating the coiled conductor from body tissue and fluids.

11. A distal end portion, as defined in claim 10, further comprising:

said insulating sheath means including projecting, foldable tines for anchoring the distal tip electrode, said insulating sheath means further including a recessed portion along said distal segment for receiving the tines in their folded condition.

12. A distal end portion, as defined in claim 9, further comprising:

projecting, foldable tines for anchoring the distal tip electrode.

* * * * *